United States Patent
Yamada et al.

(10) Patent No.: US 11,016,359 B2
(45) Date of Patent: May 25, 2021

(54) HYDROGEN OCCLUSION BODY, GASOCHROMIC LIGHT CONTROL ELEMENT, HYDROGEN SENSING ELEMENT, AND HYDROGEN SENSOR

(71) Applicants: Yasusei Yamada, Aichi (JP); Kazuki Yoshimura, Aichi (JP)

(72) Inventors: Yasusei Yamada, Aichi (JP); Kazuki Yoshimura, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 252 days.

(21) Appl. No.: 16/335,790

(22) PCT Filed: Aug. 10, 2017

(86) PCT No.: PCT/JP2017/029127
§ 371 (c)(1),
(2) Date: Mar. 22, 2019

(87) PCT Pub. No.: WO2018/055946
PCT Pub. Date: Mar. 29, 2018

(65) Prior Publication Data
US 2019/0250483 A1    Aug. 15, 2019

(30) Foreign Application Priority Data

Sep. 23, 2016  (JP) .............................. JP2016-185565

(51) Int. Cl.
*G02F 1/19* (2019.01)
*G01N 21/78* (2006.01)
(Continued)

(52) U.S. Cl.
CPC ................ *G02F 1/19* (2013.01); *B01J 23/46* (2013.01); *C01B 3/00* (2013.01); *G01N 21/783* (2013.01); *G01N 33/005* (2013.01)

(58) Field of Classification Search
CPC ... G02F 1/19; G02F 1/153; C01B 3/00; C01B 3/0005; B01J 23/46; B01J 23/44;
(Continued)

(56) References Cited

U.S. PATENT DOCUMENTS 4,132,668 A * 1/1979 Gryaznov .............. B01J 37/024
502/4
4,786,595 A   11/1988 Arai et al.
(Continued)

FOREIGN PATENT DOCUMENTS

| JP | S59-92350 | 5/1984 |
| JP | 2007-057233 | 3/2007 |

(Continued)

OTHER PUBLICATIONS

Wu et al., Mixed-phase PdRu bimetallic structures with high activity and stability for formic acid electrooxidation, 2012, Physical Chemistry Chemical Physics, No. 14, pp. 8051-8057 (Year: 2012).*

(Continued)

*Primary Examiner* — Jill A Warden
*Assistant Examiner* — John McGuirk
(74) *Attorney, Agent, or Firm* — IPUSA, PLLC (57) ABSTRACT

In one aspect of the present invention, a hydrogen occlusion body includes: a hydrogen occlusion layer containing a material whose optical property reversibly changes upon hydrogenation and dehydrogenation; and a catalyst layer containing a palladium-ruthenium alloy.

8 Claims, 8 Drawing Sheets

(51) Int. Cl.
*G01N 33/00* (2006.01)
*C01B 3/00* (2006.01)
*B01J 23/46* (2006.01)

(58) Field of Classification Search
CPC ..... B01J 23/462; G01N 21/783; G01N 33/05; G01N 2021/7773; G01N 2021/7783; G01N 21/77; G01N 21/59; Y02E 60/32
See application file for complete search history.

(56) References Cited

U.S. PATENT DOCUMENTS

| | | | |
|---|---|---|---|
| 5,635,729 | A | 6/1997 | Griessen et al. |
| 5,905,590 | A | 5/1999 | Van Der Sluis et al. |
| 6,006,582 | A | 12/1999 | Bhandari et al. |
| 6,596,236 | B2 | 7/2003 | DiMeo, Jr. et al. |
| 6,647,166 | B2 | 11/2003 | Richardson |
| 8,179,588 | B2 | 5/2012 | Yamada et al. |
| 8,758,691 | B2 | 6/2014 | Uchiyama et al. |
| 9,507,234 | B2 | 11/2016 | Yamada et al. |
| 2010/0178209 | A1 | 7/2010 | Uchiyama et al. |
| 2013/0210618 | A1* | 8/2013 | Mitlin .............. B01J 20/0248 502/302 |
| 2016/0054277 | A1 | 2/2016 | Noh et al. |

FOREIGN PATENT DOCUMENTS

| | | |
|---|---|---|
| JP | 2008-298724 | 12/2008 |
| JP | 2010-066747 | 3/2010 |
| JP | 2011-219841 | 11/2011 |
| JP | 2013-083911 | 5/2013 |
| JP | 2013-245370 | 12/2013 |
| JP | 2013245370 A * | 12/2013 |

OTHER PUBLICATIONS

Huang et al., High-performance PdRu bimetallic catalyst supported on mesoporous silica nanoparticles for phenol hydrogenation, 2014, Applied Surface Science, vol. 315, pp. 138-143 (Year: 2014).*

Korean Office Action dated Jul. 21, 2020 (Korean Patent Application No. 10-2019-7008114).
Kohei Kusada et al. "Solid Solution Alloy Nanoparticles of Immiscible Pd and Ru Elements Neighboring on Rh: Changeover of the Thermodynamic Behavior for Hydrogen Storage and Enhanced CO-Oxidizing Ability" Journal of the American Chemical Sciety, 136, pp. 1864-1871 (2014).
Extended European Search Report dated Mar. 24, 2020 (EP Patent Application No. 17852727.1).
Samhun Yun et al: "Correlations in palladium membranes for hydrogen separation; A review", Journal of Membrane Science, Elsevier BV, NL, vol. 375, No. 1, Mar. 29, 2011 (Mar. 29, 2011), pp. 28-45, XP0282092.
Gade S K et al.; "Palladium-ruthenium membranes for hydrogen separation fabricated by electroless co-deposition", International Journal of Hydrogen Energy, Elsevier Science Publishers B.V., Barking, GB, vol. 34, No. 15, Jul. 5, 2009 (Jul. 5, 2009) pp. 6484-6491, XP026375082.
Tsveta Radeva et al.: "Highly sensitive and selective visual hydrogen detectors based on YxMg1-x thin films", Sensors and Actuator B: Chemical, vol. 203, Jul. 7, 2014 (Jul. 7, 2014), pp. 745-751, XP055498744.
Marc K. Dietrich et al: "Hydrogen sorption and desorption kinetics and hydrogenation stability of Mg-metal-hydride thin films", Sensors and Actuators A; Physical, vol. 206, Dec. 17, 2013 (Jan. 17, 2013), pp. 127-131, XP055129804.
International Search Report for PCT/JP2017/029127 dated Nov. 14, 2017.
Radeva, Tsveta et al., Highly sensitive and selective visual hydrogen detectors based on Y x Mg1-x thin films, Sens Actuators B Chem, Nov. 2014, vol. 203, p. 745-751, 2.1, 2.2, 3.2, Fig.1, Fig.5.
Yasusei Yamada, "A Novel Switchable Mirror Using Gasochromic Method", Materials Science and Technology, Jun. 20, 2015(Jun. 20, 2015), vol. 52, No. 3, pp. 86 to 89, p. 88(4.2), fig.2 X.

* cited by examiner

FIG.11

HYDROGEN OCCLUSION BODY, GASOCHROMIC LIGHT CONTROL ELEMENT, HYDROGEN SENSING ELEMENT, AND HYDROGEN SENSOR

TECHNICAL FIELD

The present invention relates to a hydrogen occlusion body, a gasochromic light control element, a hydrogen sensing element, and a hydrogen sensor.

BACKGROUND ART

A hydrogen occlusion body that includes a hydrogen occlusion layer whose optical property reversibly changes upon hydrogenation and dehydrogenation; and a catalyst layer that promotes the hydrogenation and the dehydrogenation of the hydrogen occlusion layer can be used at ambient temperatures and ambient pressures. Thus, a hydrogen occlusion body as described above can be used for a gasochromic light control element that can control inflow and outflow of light and heat (see, for example, Patent Documents 1 to 5), a hydrogen sensing element (see, for example, Patent Documents 6 and 7), and a hydrogen sensor (for example, see Patent Documents 8 and 9).

As a material constituting the catalyst layer, palladium and platinum are known (for example, see Patent Document 1).

Also, as a material constituting the hydrogen occlusion layer, tungsten oxide, a rare-earth element, an alloy of magnesium and a rare-earth metal, and an alloy of magnesium and a transition metal are known (for example, see Patent Documents 2 to 7).

PRIOR ART DOCUMENTS

Patent Documents

[Patent Document 1] U.S. Pat. No. 5,635,729
[Patent Document 2] U.S. Pat. No. 5,905,590
[Patent Document 3] U.S. Pat. No. 6,647,166
[Patent Document 4] Japanese Laid-open Patent Publication No. 2010-66747
[Patent Document 5] Japanese Laid-open Patent Publication No. 2013-83911
[Patent Document 6] Japanese Laid-open Patent Publication No. 2011-219841
[Patent Document 7] Japanese Laid-open Patent Publication No. 2013-245370
[Patent Document 8] U.S. Pat. No. 6,006,582
[Patent Document 9] U.S. Pat. No. 6,596,236

DISCLOSURE OF THE INVENTION

Problem to be Solved by the Invention

However, hydrogen occlusion bodies as described above have a problem that the production cost is high because a material constituting a catalyst layer is very expensive.

In view of the above, an object in one aspect of the present invention is to reduce production cost and to provide a hydrogen occlusion body that can be used at ambient temperatures and ambient pressures.

Means for Solving the Problem

In one aspect of the present invention, a hydrogen occlusion body includes: a hydrogen occlusion layer containing a material whose optical property reversibly changes upon hydrogenation and dehydrogenation; and a catalyst layer containing a palladium-ruthenium alloy.

Effects of the Invention

According to one aspect of the present invention, it is possible to reduce production cost and to provide a hydrogen occlusion body that can be used at ambient temperatures and ambient pressures.

EMBODIMENT FOR CARRYING OUT THE INVENTION

In the following, embodiments for carrying out the present invention will be described with reference to the drawings. However, the present invention is not limited to the following embodiments, and various modifications and substitutions can be made with respect to the following embodiments without departing from the scope of the present invention.

First Embodiment

In the present embodiment, a hydrogen occlusion body according to a first embodiment of the present invention will be described. The hydrogen occlusion body according to the first embodiment of the present invention includes a hydrogen occlusion layer containing a material whose optical property reversibly changes upon hydrogenation and dehydrogenation (hereinafter referred to as "hydrogen occlusion material"), and a catalyst layer containing a palladium-ruthenium alloy.

Figure 1:
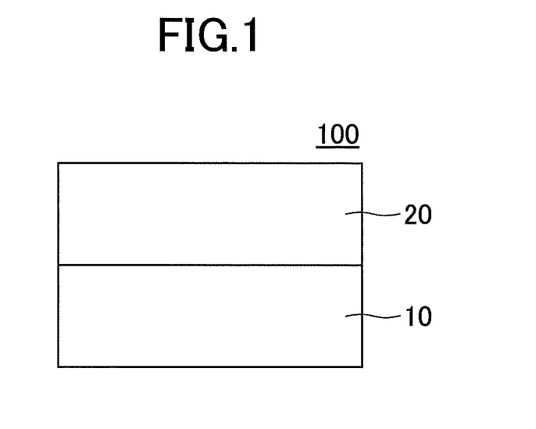
FIG. 1 is a cross-sectional view illustrating an example configuration of a hydrogen occlusion body according to a first embodiment of the present invention.

FIG. 1 illustrates a configuration example of a hydrogen occlusion body according to the first embodiment of the present invention.

The hydrogen occlusion body 100 includes a hydrogen occlusion layer 10 and a catalyst layer 20.

The hydrogen occlusion layer 10 contains a hydrogen occlusion material, and the catalyst layer 20 contains a palladium-ruthenium alloy. Therefore, the hydrogen occlusion body 100 can be used at ambient temperatures and ambient pressures.

Here, the price of ruthenium is about one tenth of that of palladium. Therefore, the hydrogen occlusion body 100 including the catalyst layer 20 containing the palladium-ruthenium alloy can reduce production cost as compared with a hydrogen occlusion body including a catalyst layer containing palladium.

The palladium-ruthenium alloy contained in the catalyst layer 20 promotes the hydrogenation and dehydrogenation of the hydrogen occlusion material contained in the hydrogen occlusion layer 10. Therefore, by the catalyst layer 20, it is possible to decrease the time required for changing the optical property of the hydrogen occlusion layer 10, that is, the switching time.

Note that the catalyst layer 20 may further contain an element other than the palladium/ruthenium alloy as a minor component (inevitable component).

Next, the palladium-ruthenium alloy will be explained.

Although the palladium-ruthenium alloy is inexpensive as the composition ratio of ruthenium is larger, the composition ratio of ruthenium is not particularly limited.

In terms of shortening the switching time in a case of storing in the atmosphere for a long time, the palladium-ruthenium alloy is preferably a compound that is represented by the general formula (1) $Pd_{1-x}Ru_x$ ($0.1<x<0.7$), and is more preferably a compound that is represented by the general formula (2) $Pd_{1-x}Ru_x$ ($0.15<x<0.55$).

The thickness of the catalyst layer 20 is appropriately selected depending on a reactivity of the hydrogen occlusion layer 10 and a catalytic ability of the palladium-ruthenium alloy, and is not particularly limited. It is preferable that thickness of the catalyst layer 20 is greater than or equal to 1 nm and less than or equal to 20 nm. When the thickness of the catalyst layer 20 is greater than or equal to 1 nm, the function of the catalyst layer 20 can be enhanced. On the other hand, when the thickness of the catalyst layer 20 is less than or equal to 20 nm, the optical transmittance of the catalyst layer 20 can be enhanced.

A method of forming the catalyst layer 20 is not particularly limited. For example, as the method of forming the catalyst layer 20, a general deposition method such as a sputtering method, a vacuum vapor deposition method, an electron beam vapor deposition method, a chemical vapor deposition (CVD) method, a plating method, or a sol-gel method may be used.

It is preferable that the hydrogen occlusion layer 10 contains a hydrogen occlusion material whose optical property reversibly changes upon hydrogenation and dehydrogenation at ambient temperatures and ambient pressures.

Next, the hydrogen occlusion material will be described.

The hydrogen occlusion material is not particularly limited as long as it is a material whose optical property reversibly changes upon hydrogenation and dehydrogenation.

Specifically, the hydrogen occlusion material may be a material having a chromic property that reversibly changes in an optical property upon hydrogenation and dehydrogenation.

As the hydrogen occlusion material, it is preferable to use a metal oxide, an organic polymer, or a metal complex whose state reversibly changes between a colored state and a transparent state upon hydrogenation and dehydrogenation, or an alloy or a hydride of a rare earth metal whose state reversibly changes between a transparent state upon hydrogenation and a reflective state (metal state) upon dehydrogenation.

Examples of metal oxides include tungsten oxide, molybdenum oxide, vanadium oxide, nickel oxide, titanium dioxide, iridium oxide, and the like.

Examples of organic polymers include polyaniline, PEDOT-PSS, polypyrrole, and the like.

Examples of metal complexes include a Prussian blue type complex and the like.

Examples of alloys include a rare earth metal-magnesium alloy such as a Y—Mg alloy, a La—Mg alloy, a Gd—Mg alloy, or a Sm—Mg alloy, a magnesium-transition metal alloy such as a Mg—Ni alloy, a Mg—Mn alloy, a Mg—Co alloy, or a Mg—Fe alloy, an alloy containing at least one element selected from elements in group 2 and two or more elements selected from elements in group 3 and rare earth elements, and the like.

Examples of hydrides of a rare earth metal include $YH_2$, $LaH_2$, $GdH_2$, $SmH_2$, and the like.

Note that the hydrogen occlusion layer 10 may further contain an element other than the hydrogen occluding material as a minor component (inevitable component).

Figure 2:
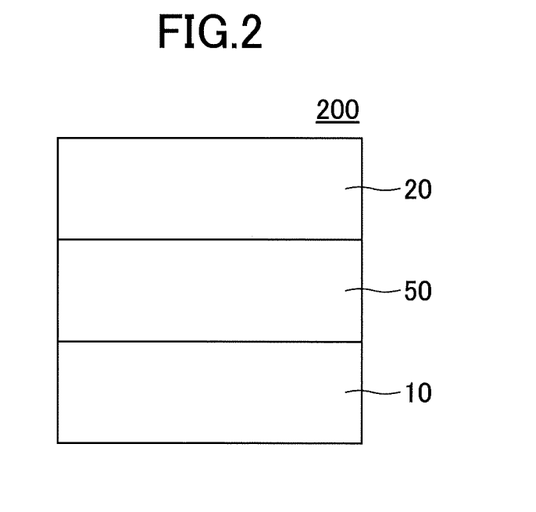
FIG. 2 is a cross-sectional view illustrating a modified example of a hydrogen occlusion body according to the first embodiment of the present invention.

Also, as illustrated in FIG. 2, a diffusion prevention layer 50 may be inserted between the hydrogen occlusion layer 10 and the catalyst layer 20 to form a hydrogen occlusion body 200.

A material constituting the diffusion prevention layer 50 is not particularly limited as long as it is able to prevent the palladium-ruthenium alloy from diffusing into the hydrogen occlusion layer 10 and being able to effectively diffuse hydrogen, which has passed through the catalyst layer 20, into the hydrogen occlusion layer 10. It is preferable to use, as a material constituting the diffusion prevention layer 50, niobium, vanadium, titanium or tantalum.

A method of forming the diffusion prevention layer 50 is not particularly limited. For example, as the method of forming the diffusion prevention layer 50, a general deposition method such as a sputtering method, a vacuum vapor deposition method, an electron beam vapor deposition method, a chemical vapor deposition (CVD) method, a plating method, or a sol-gel method can be used.

As described above, the hydrogen occlusion bodies 100 and 200 can be used at room temperatures and ambient pressures as well as reducing production cost.

Then, the hydrogen occlusion bodies 100 and 200 reversibly change in an optical property upon hydrogenation and dehydrogenation, that is, have a switching chromic property. That is, because the hydrogen occlusion bodies 100 and 200 have a function of changing the optical transmittance and the optical reflectance upon hydrogenation and dehydrogenation, the hydrogen occlusion bodies 100 and 200 can be suitably applied to a gasochromic light control element. Further, because of being able to visually determine a change in optical transmittance and optical reflectance, the hydrogen occlusion bodies 100 and 200 can be suitably applied to a hydrogen sensing element. Also, because a change in the occlusion amount of hydrogen can be estimated by measuring a change in optical transmittance and optical reflectance with a sensor or the like, the hydrogen occlusion bodies 100 and 200 can be suitably applied to a hydrogen sensing element.

Second Embodiment

In the present embodiment, a hydrogen occlusion body according to a second embodiment of the present invention will be described.

The hydrogen occlusion body according to the second embodiment of the present invention further includes a protective layer on the surface of the hydrogen occlusion body according to the first embodiment.

Figure 3:
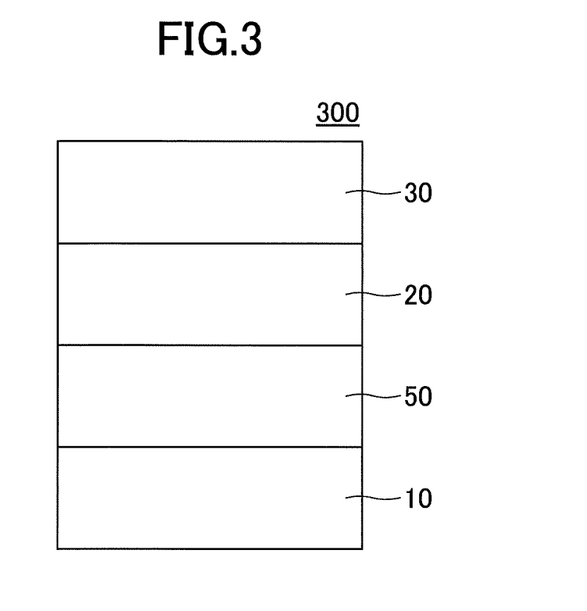
FIG. 3 is a cross-sectional view illustrating an example configuration of a hydrogen occlusion body according to a second embodiment of the present invention.

FIG. 3 illustrates a configuration example of the hydrogen occlusion body according to the second embodiment of the present invention.

The hydrogen occlusion body 300 further includes a protective layer 30 on the surface of the hydrogen occlusion body 200.

Because the configuration of the hydrogen sensing element 300 other than the protective layer 30 is similar to that of the hydrogen occlusion body 200, the description of the hydrogen sensing element 300 other than the protective layer 30 is omitted.

The hydrogen occlusion body 300 includes the protective layer 30 on at least a part of the surface of the catalyst layer 20 that is opposite to the hydrogen occlusion layer 10.

The protective layer 30 is a layer that is permeable to hydrogen, but impermeable to water and has a function of preventing, in cooperation with the catalyst layer 20, the hydrogen occlusion layer 10 from being oxidized by water or oxygen.

Although the catalyst layer 20 also has a function of preventing the hydrogen occlusion layer 10 from being oxidized, by forming the protective layer 30, the function of preventing the hydrogen occlusion layer 10 from being oxidized can be enhanced.

Further, the protective layer 30 has a function of preventing the catalyst layer 20 from being oxidized by water or oxygen.

A material constituting the protective layer 30 is not particularly limited as long as having permeability (hydrogen permeability) to hydrogen (hydrogen ions) and impermeability to water. Examples of the material constituting the protective layer 30 include a polymer such as fluororesin, polyvinyl acetate, polyvinyl chloride, polystyrene, and cellulose acetate, an inorganic material such as titanium dioxide, and the like.

For example, as a method of forming the protective layer 30, a general deposition method such as a drying method after applying a dispersion liquid in which a polymer is dispersed, a sputtering method, or a vacuum vapor deposition method for depositing an inorganic thin film can be used.

By forming the protective layer 30, the catalyst layer 20 and the hydrogen occlusion layer 10 can be prevented from being oxidized by water and oxygen. Therefore, it is possible to prevent deterioration of the catalyst layer 20 and the hydrogen occlusion layer 10 and to enhance durability.

Note that similarly to the hydrogen occlusion body 100, the diffusion prevention layer 50 may not be inserted between the hydrogen occlusion layer 10 and the catalyst layer 20.

Third Embodiment

In the present embodiment, a gasochromic light control element according to a third embodiment of the present invention will be described.

The gasochromic light control element according to the third embodiment of the present invention further includes a base material on the surface of the hydrogen occlusion body according to the first embodiment of the present invention.

The hydrogen occlusion body according to the first embodiment of the present invention has a function of reversibly changing in an optical property upon hydrogenation and dehydrogenation.

Therefore, by a change in the surrounding atmosphere, the gasochromic light control element according to the third embodiment of the present invention hydrogenates or dehydrogenates, that is, occludes or releases hydrogen. Thereby, the gasochromic light control element according to the third embodiment of the present invention can control inflow or outflow of light and heat by changing optical transmittance or optical reflectance of the hydrogen occlusion material.

Figure 4:
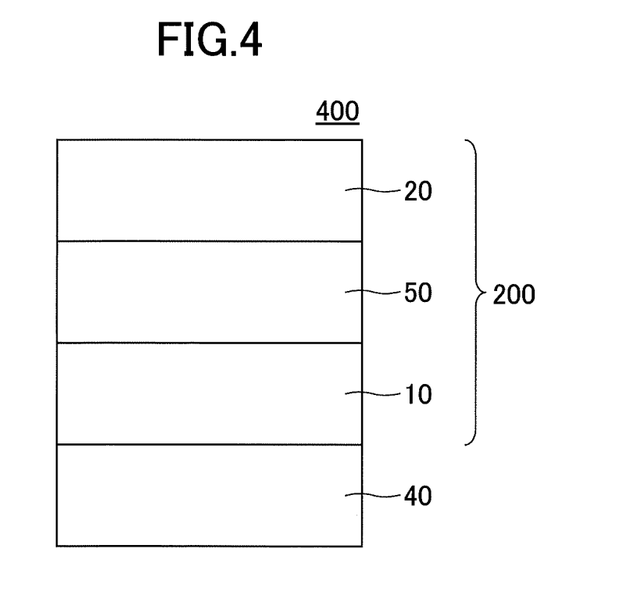
FIG. 4 is a cross-sectional view illustrating a configuration example of a gasochromic light control element according to a third embodiment of the present invention.

FIG. 4 illustrates a configuration example of a gasochromic light control element according to the third embodiment of the present invention.

The gasochromic light control element 400 further includes a base material 40 on the surface of the hydrogen occlusion body 200.

Note that since the configuration of the gasochromic light control element 400 other than the base material 40 is similar to that of the hydrogen occlusion body 200, the description of the gasochromium light control element 400 other than the base material 40 is omitted.

The gasochromic light control element 400 includes the base material 40 on at least a part of the surface of the hydrogen occlusion layer 10 of the hydrogen occlusion body 200 that is opposite to the catalyst layer 20.

Although a material constituting the base material 40 is not particularly limited as long as it is a material that transmits visible light, for example, it is preferable to use glass or plastic as the material constituting the base material 40.

Here, it is preferable to use polyethylene terephthalate (PET), polyethylene naphthalate (PEN), nylon, or acrylic as the plastic.

Figure 5:
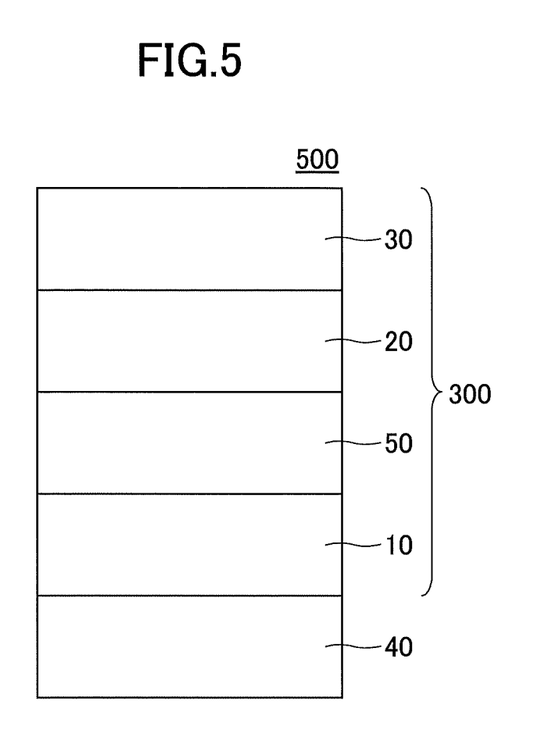
FIG. 5 is a cross-sectional view illustrating a modified example of a gasochromic light control element according to the third embodiment of the present invention.

Note that similarly to the hydrogen occlusion body 100, the diffusion prevention layer 50 may not be inserted between the hydrogen occlusion layer 10 and the catalyst layer 20. Although the gasochromic light control element, which further includes the base material on the surface of the hydrogen occlusion body according to the first embodiment of the present invention, has been described above, a gasochromic light control element that further includes a base material on the surface of the hydrogen occlusion body according to the second embodiment of the present invention may be used. That is, as illustrated in FIG. 5, a gasochromic light control element 500 in which the base material 40 is provided on at least a part of the surface of the hydrogen occlusion layer 10 that is opposite to the catalyst layer 20 of the hydrogen sensing element 300 may be used.

Fourth Embodiment

In the present embodiment, a hydrogen sensor according to a fourth embodiment of the present invention will be described.

The hydrogen sensor according to the fourth embodiment of the present invention has a configuration similar to that of the gasochromic light control element according to the third embodiment of the present invention, and further includes a base material on the surface of the hydrogen occlusion body according to the first embodiment of the present invention.

The hydrogen occlusion body according to the first embodiment of the present invention has a function of reversibly changing in an optical property upon hydrogenation and dehydrogenation.

Therefore, by measuring a change in optical transmittance or optical reflectance of the hydrogen occlusion body that occludes or release hydrogen due to a change in the surrounding atmosphere, the hydrogen sensor according to the fourth embodiment of the present invention can sense hydrogen in the atmosphere.

For example, in a case where a hydrogen sensor has a configuration similar to that of the gasochromic light control element 400 (see FIG. 4), as a method of detecting a change in optical transmittance or optical reflectance of the hydrogen occlusion layer 10, for example, it is possible to use a method of detecting reflected light or transmitted light from the base material 40 side or the catalyst layer 20 side.

In a case of a hydrogen sensor that detects transmitted light or reflected light from the base material 40 side, a material constituting the base material 40 is desirably transparent to light used for detection, that is, a material constituting the base material 40 desirably does not inhibit transmission of light used for detection.

However, in a case of a hydrogen sensor that detects reflected light from the catalyst layer 20 side, the optical property of the base material 40 is not particularly limited.

Although a material constituting the base material 40 in a case of a hydrogen sensor that detects visible light as transmitted light or reflected light from the base material 40 side is not particularly limited as long as being a material that transmits visible light, for example, it is preferable to use glass or plastic as the material constituting the base material 40.

Here, it is preferable to use polyethylene terephthalate (PET), polyethylene naphthalate (PEN), nylon, or acrylic as the plastic.

Note that similarly to the hydrogen occlusion body 100, the diffusion prevention layer 50 may not be inserted between the hydrogen occlusion layer 10 and the catalyst layer 20.

Although the hydrogen sensor, which further includes the base material on the surface of the hydrogen occlusion body according to the first embodiment of the present invention, has been described above, a hydrogen sensor that further includes a base material on the surface of the hydrogen occlusion body according to the second embodiment of the present invention may be used. That is, a configuration similar to that of the gasochromic light control element 500 (see FIG. 5) may be used.

Fifth Embodiment

Since a hydrogen sensing element according to a fifth embodiment of the present invention has a configuration similar to that of the gasochromic light control element according to the third embodiment of the present invention, a description of the fifth embodiment will not be provided.

EXAMPLES

In the following, the present invention will be described in detail with reference to Examples, but the present invention is not limited to Examples.

Examples 1 to 9

For each of following Examples, a gasochromic light control element 400 that includes a hydrogen occlusion body 200, in which a hydrogen occlusion layer 10 made of a magnesium-yttrium alloy, a diffusion prevention layer 50 made of tantalum, and a catalyst layer 20 made of a palladium-ruthenium alloy are sequentially stacked on a glass substrate as a base material 40, was prepared.

Specifically, on the glass substrate (base material 40) having a thickness of 1 mm, a magnesium-yttrium alloy thin film (hydrogen occlusion layer 10) having a film thickness of 50 nm, a tantalum thin film (diffusion prevention layer 50) having a film thickness of nm, a palladium-ruthenium alloy thin film (catalyst layer 20) having a film thickness of 3 nm with a composition ratio changed were sequentially deposited.

Next, deposition conditions of the hydrogen occlusion layer 10, the diffusion prevention layer 50, and the catalyst layer 20 will be described. When depositing the magnesium-yttrium alloy thin film of the hydrogen occlusion layer 10, the tantalum thin film of the diffusion prevention layer 50, and the palladium-ruthenium alloy thin film of the catalyst layer 20, a magnetron sputtering equipment with multi-targets was used. At this time, for five sputter guns, metallic magnesium, metallic yttrium, metallic tantalum, metallic palladium and metallic ruthenium were respectively set as targets.

First, after cleaning the glass substrate (base material 40), the glass substrate was set in a vacuum apparatus, and the inside of the chamber is evacuated.

Next, by simultaneously applying power of 10 W and 30 W to the respective targets of metallic magnesium and metallic yttrium, a magnesium-yttrium alloy thin film (hydrogen occlusion layer 10) that is represented by a composition formula $Mg_{0.4}Y_{0.6}$ was deposited. At this time, sputtering was carried out by setting the argon gas pressure in the sputtering to 0.3 Pa and applying it to each target for a predetermined time by a DC sputtering method.

Note that the composition ratio of the magnesium-yttrium alloy thin film (hydrogen occlusion layer 10) to be deposited can be controlled based on the electric power applied to the respective targets. Also, the film thickness of the magnesium-yttrium alloy thin film (hydrogen occlusion layer 10) to be deposited can be controlled based on the duration by which power is applied to the targets.

Next, under the same vacuum condition as the deposition of the hydrogen occlusion layer 10, the tantalum thin film (diffusion prevention layer 50) was deposited by applying 20 W of power to the target of metallic tantalum.

Next, by simultaneously applying power to the targets of metallic palladium and metallic ruthenium, a palladium-ruthenium alloy thin film (catalyst layer 20) that is represented by a composition formula $Pd_{1-x}Ru_x$ (x=0.1, 0.2, 0.3, 0.4, 0.5, 0.6, 0.7, 0.8, 0.9) was deposited to prepare the gasochromic light control element 400 including the hydrogen occlusion body 200 for each of Examples 1 to 9.

Comparative Example 1

With the exception of applying power only to metallic palladium to make x=0, that is, a palladium thin film (catalyst layer 20) was formed, a gasochromic light control element 400 including a hydrogen occlusion body 200 was prepared similarly to Examples 1 to 9.

Table 1 indicates, for each of Examples 1 to 9 and Comparative Example, the power applied to the targets when depositing the catalyst layer 20 in the gasochromic light control element 400, and the composition ratio of the catalyst layer 20.

TABLE 1

| | CATALYST LAYER 20 | | |
|---|---|---|---|
| | POWER [W] | | COMPOSITION |
| | Pd | Ru | RATIO |
| Example 1 | 27.0 | 4.5 | $Pd_{0.90}Ru_{0.10}$ |
| Example 2 | 24.0 | 9.0 | $Pd_{0.80}Ru_{0.20}$ |
| Example 3 | 21.0 | 13.5 | $Pd_{0.70}Ru_{0.30}$ |
| Example 4 | 18.0 | 18.0 | $Pd_{0.60}Ru_{0.40}$ |
| Example 5 | 15.0 | 22.5 | $Pd_{0.50}Ru_{0.50}$ |
| Example 6 | 12.0 | 27.0 | $Pd_{0.40}Ru_{0.60}$ |
| Example 7 | 9.0 | 31.5 | $Pd_{0.30}Ru_{0.70}$ |
| Example 8 | 6.0 | 36.0 | $Pd_{0.20}Ru_{0.80}$ |
| Example 9 | 3.0 | 40.5 | $Pd_{0.10}Ru_{0.90}$ |
| Comparative Example 1 | 30.0 | 0.0 | Pd |

[Gasochromic Property]

The gasochromic light control elements 400 prepared by the procedure as described above were in a reflective state of metallic luster. Furthermore, even when left in the atmosphere for 500 hours, the gasochromic light control elements 400 were similarly in a reflective state of metallic luster. Upon exposing the surface of the palladium-ruthenium alloy thin film to hydrogen gas of 1 atm diluted with argon to be at 4 vol % (hereinafter referred to as "hydrogen-containing gas"), the state changed to a transparent state by the magnesium-yttrium alloy thin film occluding hydrogen, that is, by hydrogenation. In this state, upon exposing the surface of the palladium-ruthenium alloy thin film to the atmosphere, the state returned to the reflective state by releasing hydrogen, that is, by dehydrogenation. As described above, the optical property of the gasochromic light control elements 400 changed due to occlusion and release of hydrogen at ambient temperatures and normal pressures, that is, due to hydrogenation and dehydrogenation.

On the other hand, the period of time to become the transparent state by occluding hydrogen, that is, by hydrogenation, and the period of time to become the reflective state by releasing hydrogen, that is, by dehydrogenation were greatly changed due to the composition ratio of the palladium-ruthenium alloy.

[Optical Transmittance]

After the gasochromic light control element 400 was left in the atmosphere for 500 hours, the optical transmittance of the gasochromic light control element 400 was measured.

Figure 6:
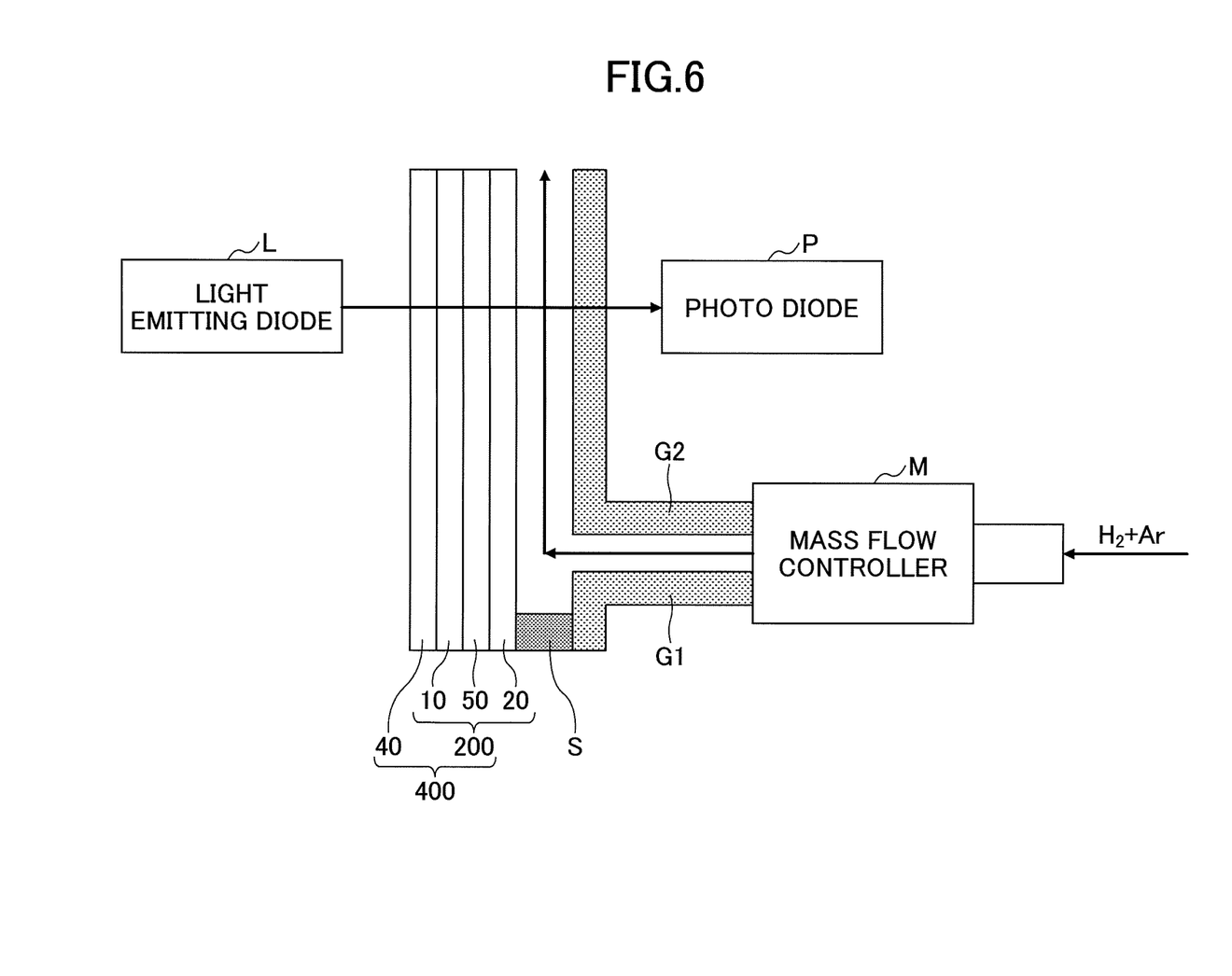
FIG. 6 is a cross-sectional view illustrating a configuration of a measurement apparatus of optical transmittance.
Figure 7A:
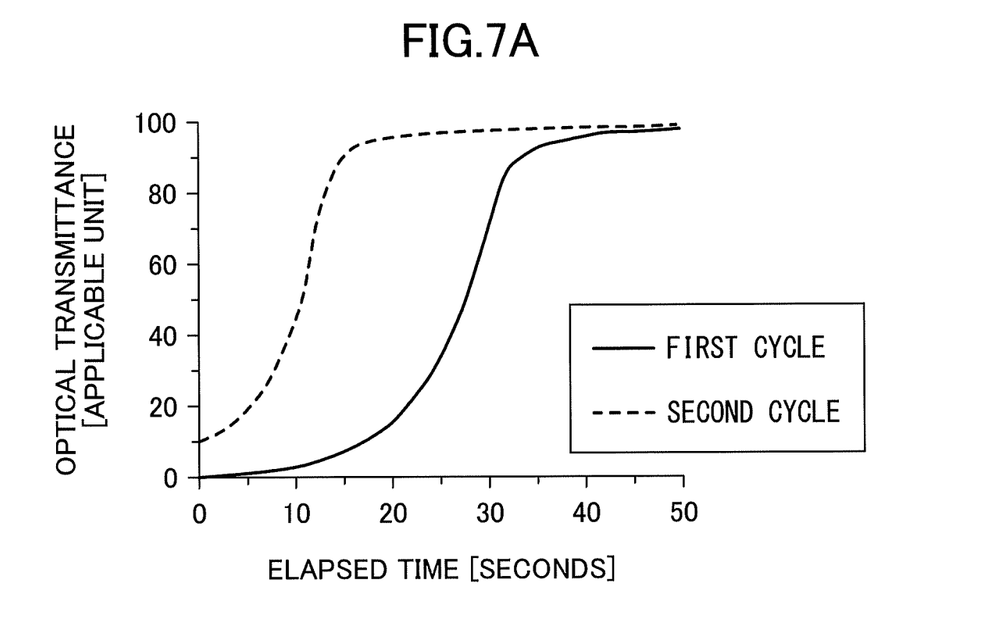
FIG. 7A is a diagram illustrating a measurement result of optical transmittance of a gasochromic light control element of Comparative Example 1.
Figure 7B:
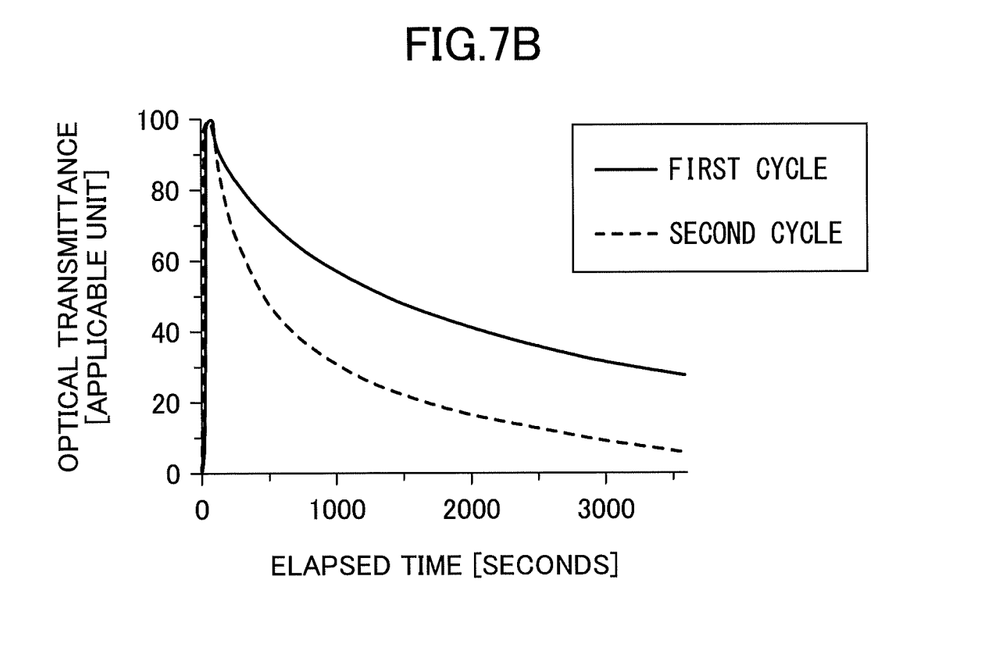
FIG. 7B is a diagram illustrating the measured result of optical transmittance of the gasochromic light control element of Comparative Example 1.
Figure 8A:
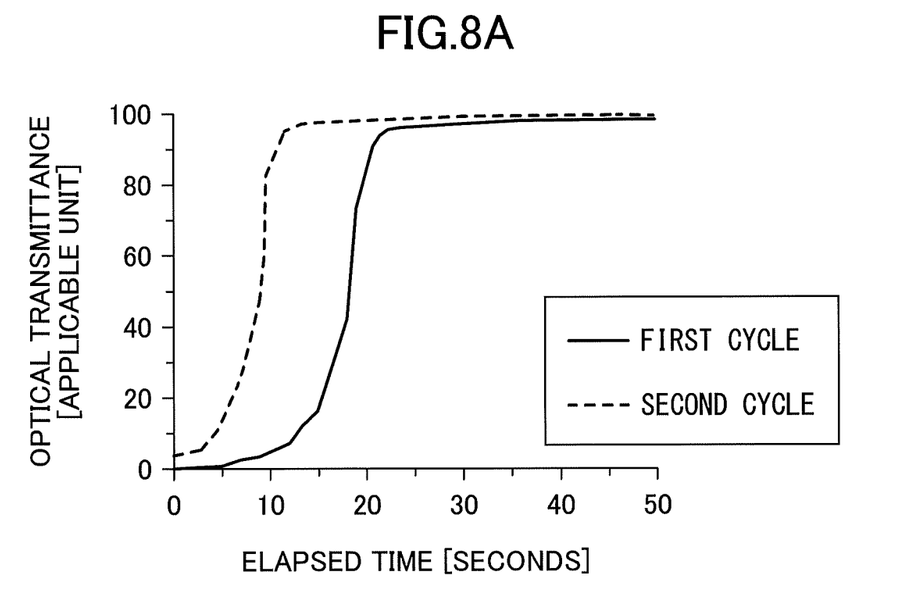
FIG. 8A is a diagram illustrating the measured result of optical transmittance of a gasochromic light control element of Example 2.
Figure 8B:
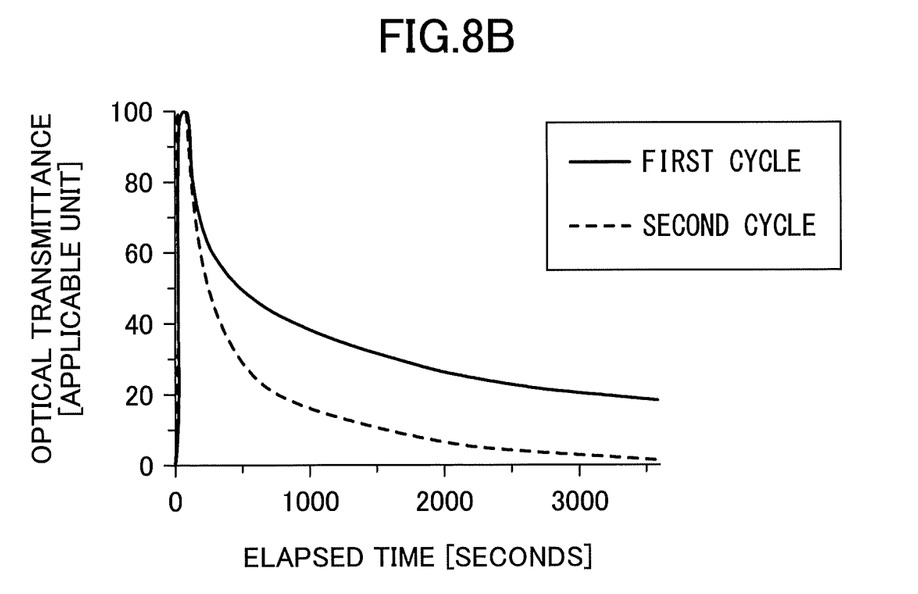
FIG. 8B is a diagram illustrating the measured result of optical transmittance of the gasochromic light control element of Example 2.
Figure 9A:
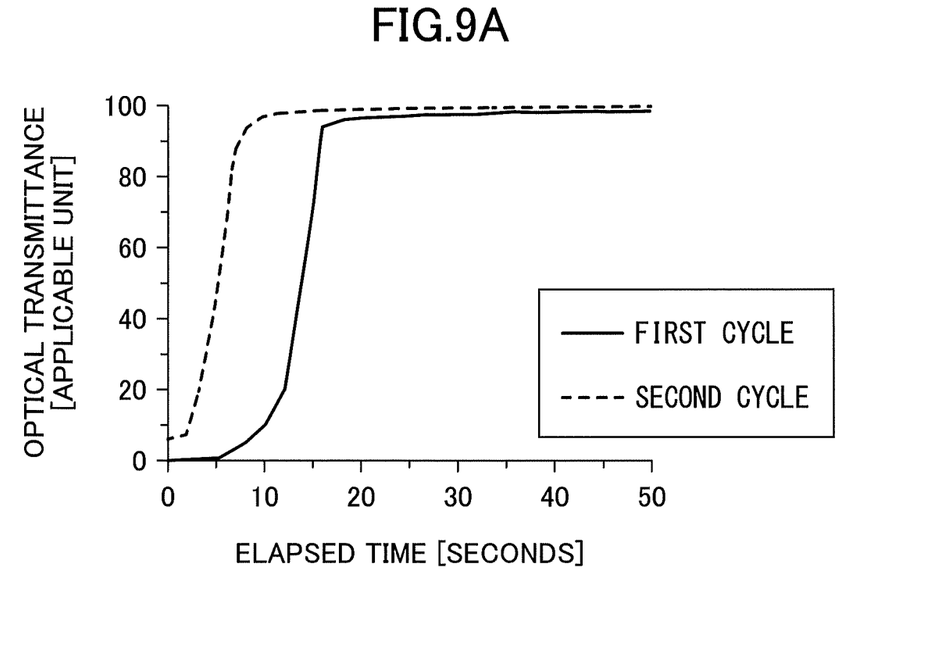
FIG. 9A is a diagram illustrating the measured result of optical transmittance of a gasochromic light control element of Example 4.
Figure 9B:
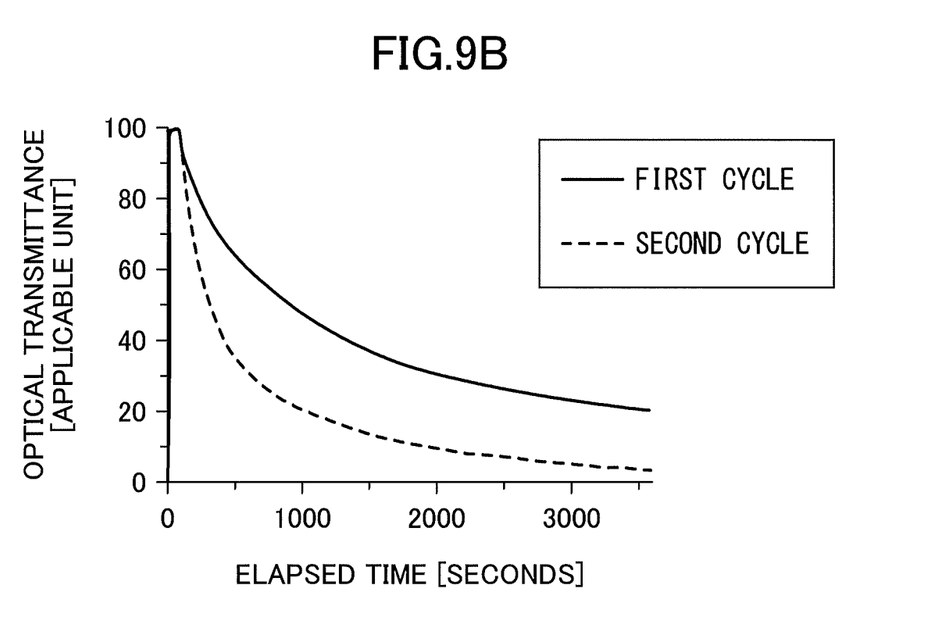
FIG. 9B is a diagram illustrating the measured result of optical transmittance of the gasochromic light control element of Example 4.

Specifically, as illustrated in FIG. 6, a glass plate G1 having a thickness of 1 mm was attached to the gasochromic light control element 400 via a spacer S. Next, after a flow of a predetermined amount of hydrogen-containing gas was performed for 95 seconds by a mass flow controller M in the gap between the glass plate G1 and the glass plate G2 having a thickness of 1 mm, and the flow of the hydrogen-containing gas was stopped for sixty minutes. When the flow of the hydrogen-containing gas is stopped, air flows into the gap between the two glass plates G1 and G2 from an opening portion. The flow control of the hydrogen-containing gas with this operation as one cycle was repeated for a predetermined number of times, during which the optical transmittance was measured every 2 seconds. As a light source, a light emitting diode L having a wavelength of 940 nm was used, and as a light receiving element, a photodiode P was used.

FIG. 7A, FIG. 7B, FIG. 8A, FIG. 8B, FIG. 9A, and FIG. 9B illustrate measured results of the optical transmittances of the gasochromic light control elements 400 of Comparative Example 1 and Examples 2 and 4. Here, A and B are respectively the case in which the state changes from the reflective state to the transparent state and the case in which the state changes from the transparent state to the reflective state.

Note that in FIG. 7A, FIG. 7B, FIG. 8A, FIG. 8B, FIG. 9A, and FIG. 9B, the elapsed time means a time elapsed from the start or stop of the flow of the hydrogen-containing gas.

Also, the optical transmittance other than that when changing from the reflective state to the transparent state in the first cycle was normalized such that the lowest value among the optical transmittance values of eight times reflective states excluding the optical transmittance of the reflective state immediately after deposition was 0 [applicable unit] and the optical transmittance that become constant in the transparent state was 100 [applicable unit].

However, the optical transmittance when changing from the reflective state to the transparent state in the first cycle was normalized such that the optical transmittance immediately after deposition was 0 [applicable unit] and the optical transmittance that become constant in the transparent state was 100 [applicable unit].

It can be seen from FIG. 7A, FIG. 7B, FIG. 8A, FIG. 8B, FIG. 9A, and FIG. 9B that in the gasochromic light control elements 400 of Comparative Example 1 and Examples 2 and 4, the switching time is shorter in the second cycle than in the first cycle. Furthermore, it can be seen that in the gasochromic light control elements 400 of and Examples 2 and 4, the switching time from the reflective state to the transparent state and the switching time from the transparent state to the reflective state are shorter than those of the gasochromic light control element 400 of Comparative Example 1.

Here, the time from the start of the flow of hydrogen-containing gas to when the optical transmittance has reached 90 [applicable unit] is defined as the switching time from the reflective state to the transparent state. Also, the time from the stop of the flow of hydrogen-containing gas to when the optical transmittance has reached 10 [applicable unit] is defined as the switching time from the transparent state to the reflective state.

Figure 10:
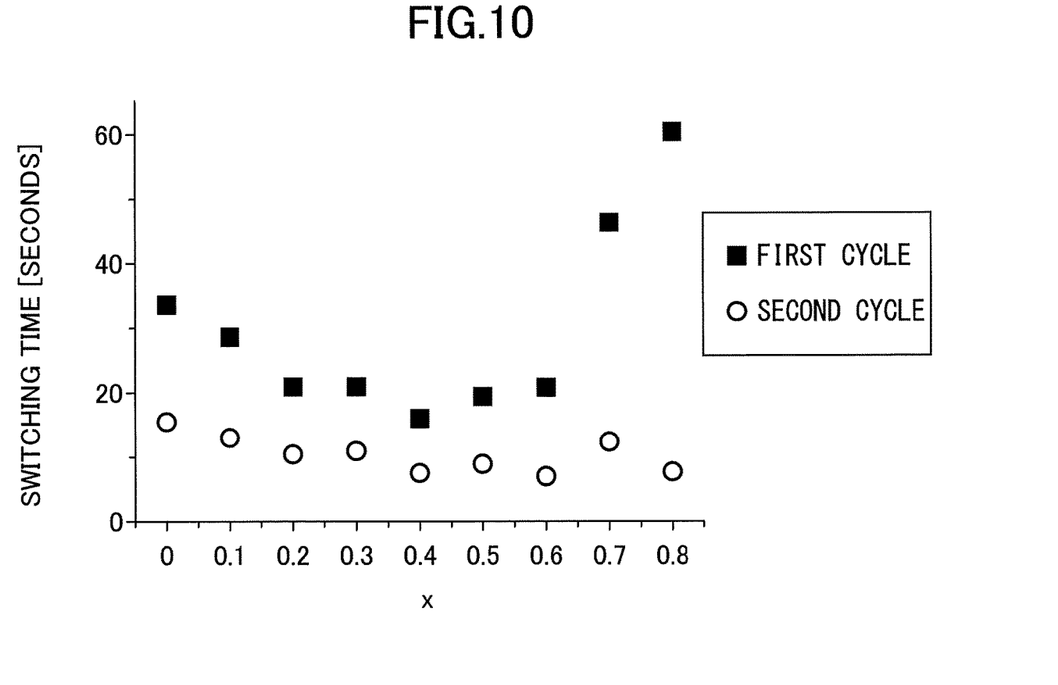
FIG. 10 is a diagram illustrating the relationship of a switching time from a reflective state to a transparent state with respect to a composition ratio of a palladium-ruthenium alloy.
Figure 11:
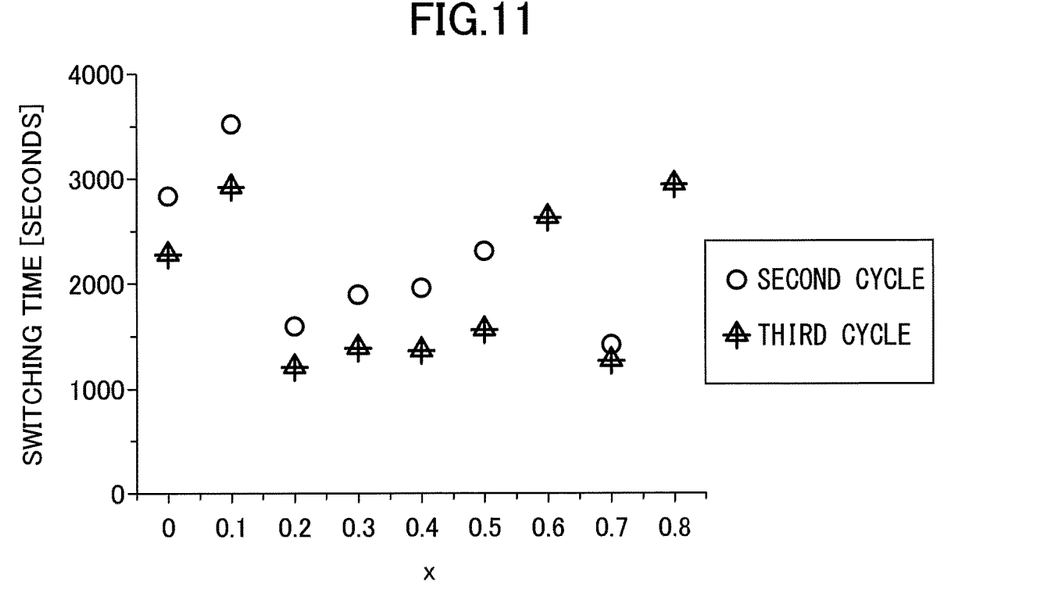
FIG. 11 is a diagram illustrating the relationship between a switching time from the transparent state to the reflective state with respect to the composition ratio of the palladium-ruthenium alloy.

FIG. 10 and FIG. 11 respectively illustrate the relationship between the switching time from the reflective state to the transparent state and x in the composition formula described above and the relationship between the switching time from the transparent state to the reflective state and x in the composition formula described above.

Note that in FIG. 10 and FIG. 11, because the switching time of x=0.9 was 3600 seconds or more, the switching time of x=0.9 is omitted.

Also, in FIG. 11, because the switching times of x=0.6 and 0.8 in the first cycle and the second cycle were 3600 seconds or more, they are omitted.

It can been seen from FIG. 10 and FIG. 11, that the switching time is short when the formula $0.1<x<0.6$ is satisfied. It is considered that this is because, by alloying with ruthenium, the catalytic action of palladium is not degraded even being left in the atmosphere.

The present international application is based on and claims priority to Japanese Patent Application No. 2016-185565, filed on Sep. 23, 2016, the entire contents of Japanese Patent Application No. 2016-185565 are hereby incorporated herein by reference.

DESCRIPTION OF REFERENCE SYMBOLS

10 Hydrogen occlusion layer
20 catalyst layer
30 Protective layer
40 Base material
50 Diffusion prevention layer
100, 200, 300 Hydrogen occlusion body
400, 500 gasochromic light control element

The invention claimed is:

1. A hydrogen occlusion body comprising:
   a hydrogen occlusion layer containing a material whose optical property reversibly changes upon hydrogenation and dehydrogenation; and
   a catalyst layer containing a palladium-ruthenium alloy, wherein the palladium-ruthenium alloy is represented by a general formula $Pd_{1-x}Ru_x$ where $0.15<x<0.55$.

2. The hydrogen occlusion body according to claim 1, wherein the material whose optical property reversibly changes is a magnesium-yttrium alloy.

3. The hydrogen occlusion body according to claim 1, further comprising:
   a diffusion prevention layer that is provided between the hydrogen occlusion layer and the catalyst layer and that is constituted by a material selected from a group consisting of niobium, vanadium, titanium, or tantalum.

4. The hydrogen occlusion body according to claim 1, wherein a thickness of the catalyst layer is greater than or equal to 1 nm and less than or equal to 20 nm.

5. The hydrogen occlusion body according to claim 1, further comprising:
   a protective layer provided opposite the hydrogen occlusion layer with respect to the catalyst layer.

6. A gasochromic light control element comprising:
   the hydrogen occlusion body according to claim 1.

7. A hydrogen sensing element comprising the hydrogen occlusion body according to claim 1.

8. A hydrogen sensor comprising the hydrogen occlusion body according to claim 1.

\* \* \* \* \*